(12) United States Patent
Portney

(10) Patent No.: US 6,428,545 B2
(45) Date of Patent: *Aug. 6, 2002

(54) INTRAOCULAR LENS IMPLANTING INSTRUMENT

(75) Inventor: Valdemar Portney, Tustin, CA (US)

(73) Assignee: Allergan Sales, INC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/917,467

(22) Filed: Jul. 28, 2001

Related U.S. Application Data

(63) Continuation of application No. 09/565,894, filed on May 5, 2000, now Pat. No. 6,283,976.

(51) Int. Cl.⁷ .................................................. A61F 9/00
(52) U.S. Cl. ..................................... 606/107; 623/6.12
(58) Field of Search .......................... 606/107, 1, 161, 606/167; 623/6.12, 6.63, 4.1; 604/293, 294, 59

(56) References Cited

U.S. PATENT DOCUMENTS

| | | | |
|---|---|---|---|
| 4,681,102 A | 7/1987 | Bartell | |
| 5,123,905 A | 6/1992 | Kelman | |
| 5,354,333 A | * 10/1994 | Kammann et al. | 623/6.12 |
| 5,902,307 A | * 5/1999 | Feingold et al. | 606/107 |
| 5,944,725 A | * 8/1999 | Cicenas et al. | 606/107 |
| 5,947,976 A | * 9/1999 | Van Noy et al. | 606/107 |
| 6,001,107 A | * 12/1999 | Feingold | 606/107 |
| 6,162,229 A | * 12/2000 | Feingold et al. | 606/107 |
| 6,283,976 B1 | * 9/2001 | Portney | 606/107 |

FOREIGN PATENT DOCUMENTS

| | | |
|---|---|---|
| EP | 0340698 | 11/1989 |
| EP | 0392773 | 10/1990 |
| FR | 2789890 | 8/2000 |
| WO | 95/24863 | 9/1995 |
| WO | 97/15253 | 5/1997 |

* cited by examiner

Primary Examiner—Pedro Philogene
(74) Attorney, Agent, or Firm—Stout, Uxa, Buyan & Mullins, LLP; Frank J. Uxa

(57) ABSTRACT

An instrument for implanting an elastically foldable intraocular lens in an eye is described. The instrument comprises a barrel having proximal and distal ends and a nozzle having a slender ocular insertion end region sized for insertion through an ocular incision no greater than about 3.7 mm., the nozzle being attached to the distal end of the nozzle. The barrel includes an intraocular lens holding chamber upstream of the nozzle. First and second shield elements are disposed inside along opposite side regions of the nozzle, each of the shield elements having an elastically deformable protective shield region disposed in the nozzle in an elastically deformed state. A mechanism is described for enabling the sequential pushing of the protective shield regions axially out of the nozzle insertion end region for expanding into their undeformed shape, the pushing of an elastically deformed intraocular lens axially out of the nozzle insertion end region for expanding into its undeformed state between the protective shield regions, and the pulling of the protective shield regions back into the nozzle insertion end region. The protective shield regions are generally paddle-shaped having a thickness of about 0.15 mm in their undeformed state and at least one of the protective shield regions having a width of about 5 mm in an undeformed state.

20 Claims, 5 Drawing Sheets

INTRAOCULAR LENS IMPLANTING INSTRUMENT

This is a continuation of application Ser. No. 09/565,894 filed May 5, 2000 now U.S. Pat. No. 6,283,976.

BACKGROUND OF THE INVENTION

1. Field of the Invention

The present invention relates generally to the field of ophthalmics, more particularly to intraocular lenses (IOLs), and still more particularly to instruments for implanting IOLs in eyes.

2. Background Discussion

It may helpful to the understanding of the present invention to define the terms "phakic" and "aphakic" as relates to human eyes. The term "phakic" applies to eyes in which the natural ocular lens is still present. This is in contrast to "aphakic" that applies to eyes from which the natural lens has—for any reason—been removed.

A phakic eye is considered a dynamic or active eye because the living, natural lens is subject to change over time. In contrast, an aphakic eye is considered a static eye because the natural ocular lens has been removed. Vision in a normal eye is enabled by light from a viewed image being refracted to the retina by the cornea and the natural lens located between the cornea and the retina.

A relatively common ocular problem is impaired or complete loss of vision due to the natural lens becoming cloudy or opaque—a condition known as cataract. The formation of cataracts is typically associated with natural bodily aging, for example, due to prolonged exposure to ultraviolet light, and most individuals over the age of about 60 years suffer from cataracts at least to some extent.

So far as is known, cataracts cannot currently be cured, reversed, or even significantly arrested. Accordingly, corrective action for serious cataracts involves surgically removing the natural lens when the lens becomes so cloudy that vision is substantially impaired. The result is that a phakic eye then becomes an aphakic eye.

After a defective natural lens has been surgically removed, the current (since about the 1940's) vision-restoring procedure is to implant in the aphakic eye an artificial, refractive replacement lens called an intraocular lens (IOL) having an optic and optic fixation means. Previously (and in some cases, still), thick, heavy, high diopter spectacles were prescribed for aphakic eyes. Such spectacles however were and still are generally disliked by most aphakic individuals for their weight and unsightly appearance.

Until relatively recently, IOLs for aphakic eyes were typically made from rigid polymethyl methacrylate (PMMA), a hard, biocompatible, plastic material. Within the past few years, however, the manufacture of IOL's has largely shifted from rigid PMMA to soft, elastically deformable silicone or acrylic material that enables insertion of folded (or otherwise dimensionally-reduced) IOLs through substantially smaller ocular incisions that those required for the implanting of rigid IOL's. Such smaller ocular incisions typically minimize patient trauma, reduce the risk of surgical complications and speed post-surgical recovery.

In addition to continuing interest in implanting IOL's in aphakic eyes, attention has recently been given to the implanting of IOL's in otherwise healthy phakic eyes to correct such common vision problems as myopia, hyperopia, presbyopia and astigmatism.

This implanting of corrective IOLs in phakic eyes is an often-attractive alternative to the wearing of corrective spectacles or contact lenses, which limit certain activities and even certain professions, or having performed such ocular surgical procedures on the cornea as radial keratomy (RK), photo-radial keratectomy (PRK) or LASIK, which may not be desired by or contra-indicated for some individuals.

In fact, the implanting of corrective IOLs in phakic eyes to correct vision problems is considered by many in the field of ophthalmics to be one of the remaining frontiers of vision correction.

Although aphakic IOL's are almost always implanted in the posterior chamber of the eye from which the natural lens has been removed, corrective IOL's for phakic eyes are usually implanted in the anterior chamber of the eye between the cornea and the iris.

The small anterior chamber axial dimension-typically only about 2 mm—between the posterior (rear) surface of the cornea and the anterior (front) surface of the iris, requires that anterior chamber IOL's typically be very thin to avoid undesirable contact with the easily-damaged endothelial layer of the cornea.

Elastically deformable IOL's are introduced into the eye, in this case, the anterior chamber of the eye, through some type of small injector nozzle in which the IOL's are folded or deformed to pass through and out of the nozzle after the nozzle has been inserted through a small ocular incision. As the deformed IOL'S are pushed out of the nozzle tip, they elastically unfold, typically, in an uncontrolled manner, to regain their original optical shape. However, uncontrolled unfolding of IOL's in the anterior chamber creates a serious risk of the IOL's contacting and injuring the sensitive endothelial surface of the cornea, thereby possibly causing a new vision problem.

Accordingly, a principal objective of the present invention is to provide an IOL implanting (insertion) instrument that provides precisely controlled unfolding of an elastically deformed IOL after the IOL has been introduced into an eye, particularly, the anterior chamber of an eye. It will be appreciated, however, that the IOL implanting instrument can also be used for the implanting of an elastically deformable IOL in the posterior chamber of an eye.

SUMMARY OF THE INVENTION

In accordance with the present invention, there is provided an instrument for implanting an elastically deformable intraocular lens in an eye. The IOL implanting instrument comprises a nozzle having a slender ocular insertion end region and at least one shield element having a protective shield region disposed in a deformed condition in the nozzle. Further included are operating means for enabling the sequential (i) pushing of the at least one deformed protective shield region axially out of the nozzle insertion end region for expanding into its undeformed shape, and (ii) pushing of an elastically deformed intraocular lens axially out of the nozzle insertion end region for expanding into its undeformed shape adjacent said protective shield region.

The operating means include at least one actuating pin, a distal end of the at least one actuating pin being connected to the at least one shield element. The operating means also include a piston and an intraocular lens pushing member attached to a distal end of the piston. Further, the operating means include pushing member and means for selectively coupling the pushing member to the at least one actuating pin or to the piston.

Preferably, the at least one shield element includes first and second shield elements having protective shield regions disposed in opposite side regions of the nozzle. In such case, the operating means enables the sequential (i) pushing of the protective shield regions of the first and second shield elements axially out of the nozzle insertion end region for expanding into their undeformed shape, and (ii) pushing of an elastically deformed intraocular lens axially out of the nozzle insertion end region for expanding into its undeformed shape between the protective shield regions.

In accordance with a preferred embodiment of the invention, an instrument for implanting an elastically foldable intraocular lens in an eye comprises a nozzle is having a slender ocular insertion end region and first and second shield elements. The first element has a first, elastically deformable protective shield region and the second shield element has a second elastically deformable protective shield region, the first and second protective shield regions being disposed in opposite side regions of the nozzle in a deformed state.

Further comprising the instrument are operating means for enabling the sequential (i) pushing of the protective shield regions axially out of the nozzle insertion end region for expanding into their undeformed state, (ii) pushing an elastically deformed intraocular lens axially out of the nozzle insertion end region for expanding into its undeformed state between the protective shield regions, and (iii) pulling the protective shield regions back into said nozzle insertion end region after the elastically deformed intraocular lens has expanded between the protective shield regions.

The preferred IOL implanting instrument includes a tubular barrel and means for detachably attaching the nozzle to a distal end of the barrel. An intraocular lens holding chamber is located in the barrel upstream of the nozzle. The operating means include first and second actuating pins longitudinally disposed in the barrel, distal ends of the first and second pins being connected to respective ones of the first and second shield elements, and further include a piston axially disposed in the barrel and an intraocular lens pushing member attached to a distal end of the piston.

The operating means include a pushing member and means for selectively coupling the pushing member to either the first and second actuating pins or to the piston. The protective shield regions of the first and second shield elements are initially curled up in the nozzle and are preferably constructed of a material selected from a group consisting of silicone and acrylic materials and are generally paddle-shaped in an undeformed condition. The protective shield regions have a preferred thickness of about 0.15 mm in the undeformed condition and at least one of the protective shield regions has a width of about 5 mm in the undeformed condition.

The nozzle ocular insertion end region is sized for insertion through an ocular incision no greater than about 3.7 mm.

Accordingly, an instrument for implanting an elastically foldable intraocular lens in an eye comprises a barrel having proximal and distal ends; a nozzle, having a slender ocular insertion end region sized for insertion through an ocular incision no greater than about 3.7 mm, attached to the distal end of the nozzle; an intraocular lens holding chamber in the barrel upstream of the nozzle; and first and second shield elements into and along opposite side regions of the nozzle, each of the first and second shield elements having an elastically deformable protective shield region disposed in the nozzle in an elastically deformed state.

Operating means are included for enabling the sequential pushing of the first and second shield element shield regions axially out of the nozzle insertion end region for expanding into their undeformed shape, the pushing of an elastically deformed intraocular lens axially out of the nozzle insertion end region for expanding into its undeformed state between the first and second shield element protective shield regions, and the pulling of the protective shield regions back into the nozzle insertion end region.

The operating means include first and second actuating pins longitudinally disposed in the barrel, distal ends of the first and second pins being connected to respective ones of first and second shield elements and further include a piston axially disposed in the barrel and an intraocular lens pushing member attached to a distal end of the piston. The operating means further include a pushing member and means for selectively coupling the pushing member to the first and second actuating pins or to the piston.

The protective shield regions of the first and second shield elements are generally paddle-shaped having a thickness of about 0.15 mm in their undeformed state, and at least one of the first and second element protective shield regions has a width of about 5 mm in its undeformed state.

By expanding an elastically deformed intraocular lens dispensed into an anterior chamber from an injection nozzle between the deployed protective shield regions, the expanding of the intraocular lens is confined between the shield regions. Thus the protective shield regions protect the sensitive and easily injured endothelial surface of the cornea from possible damage by an uncontrolled expansion of an implanted elastically deformed intraocular lens.

BRIEF DESCRIPTION OF THE DRAWINGS

The present invention can be more readily understood by a consideration of the following detailed description when taken in conjunction with the accompanying drawings, in which.

In the various FIGS., the same elements and features are given the same reference numbers.

DESCRIPTION OF THE PREFERRED EMBODIMENT

Figure 1:
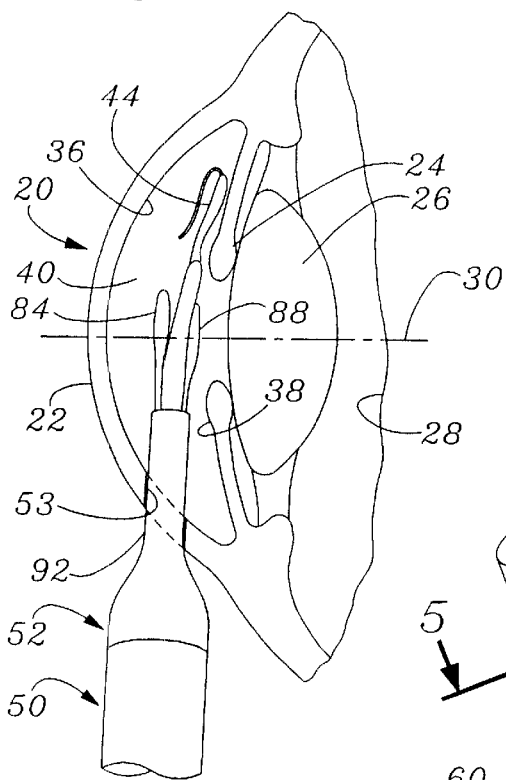
FIG. 1 is a simplified drawing of a human phakic eye, showing a cornea, an iris, an anterior chamber between the cornea and iris and showing a natural lens in a posterior chamber rearward of the iris, and further depicting an intraocular lens in the process of being implanted in the anterior chamber by use of the intraocular lens implanting instrument of the present invention.

There is depicted in FIG. 1, a forward region 20 of a typical human phakic eye. Shown generally comprising forward region 20 of the depicted eye are a cornea 22, an iris 24, a natural lens 26 located in a posterior chamber 28 and an optic axis 30. Located between a posterior (endothelium) surface 36 of cornea 22 and an anterior surface 38 of iris 24 is an anterior chamber 40 of the eye region 20.

Further depicted in FIG. 1, by way of illustration, is an intraocular lens (IOL) 44 in the process of being implanted in anterior chamber 40 by an IOL implanting instrument 50 of the present invention (more particularly described below, an IOL insertion nozzle 52 of which is shown extending through a corneal incision 53.

It is to be understood, however, although a forward region 20 of a phakic eye is depicted in FIG. 1, instrument 50 is in no way limited to the implanting of IOL's 44 in anterior chamber 40 of a phakic eye. The present instrument 50 is also applicable to implanting an IOL in the anterior chamber of an aphakic eye, and may alternatively be used for the implanting of IOL's in the posterior chamber of a phakic or an aphakic eye.

Figure 2:
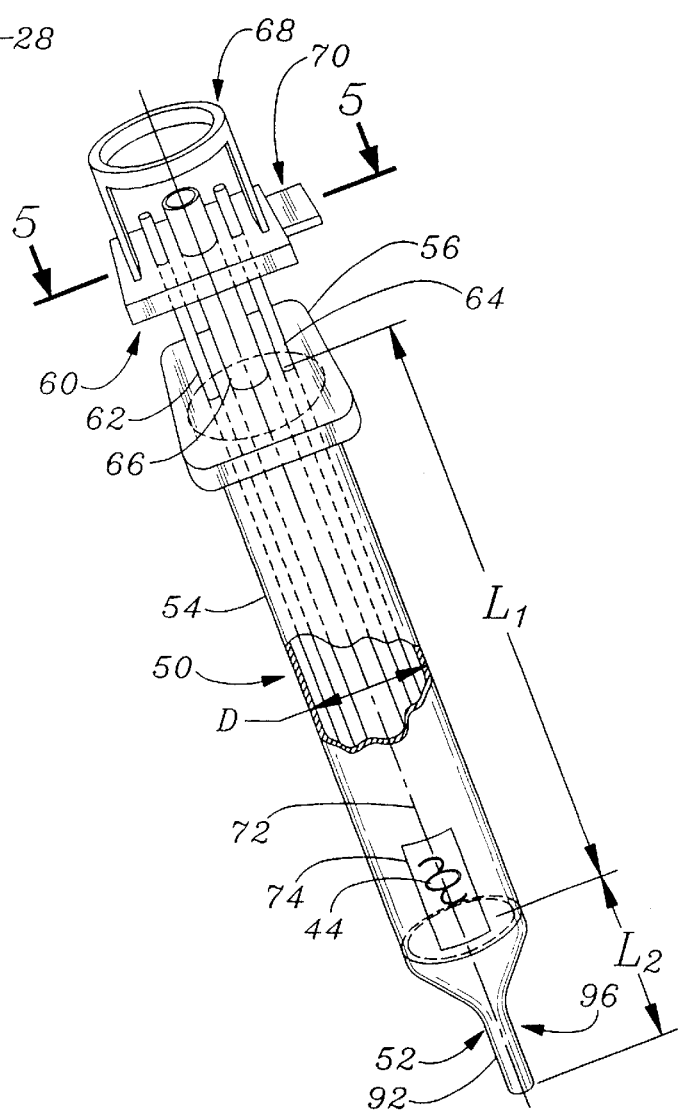
FIG. 2 is a partially cut-away perspective drawing of the intraocular lens implanting instrument of the present invention, showing a barrel, a detachable lens insertion nozzle, and operating portions of the instrument.

As illustrated in FIG. 2, IOL implanting instrument 50, which outwardly resembles a syringe, comprises, in addition to above-mentioned IOL insertion nozzle 52, an elongate, hollow, cylindrical barrel 54 to a distal end of which is attached the insertion nozzle. Nozzle 52 is preferably constructed as a single-use, disposable device and is, therefore, preferably detachably attached to barrel 54, as by a conventional leur, friction fitting (not shown) of the type commonly used for attaching needles to surgical syringes.

Attached to a proximal end of barrel is a flange 56 for engaging an instrument user's fingers for operation of instrument 50. Further included, as more particularly described below, are instrument operating means 60 which comprise slender first and second shield element operating pins or rods 62 and 64, a IOL pushing piston 66, a thumb-operated plunger or pushing member 68 and a mechanical selecting means 70 for enabling the selective connection of the plunger to either the two shield operating pins or the piston during an IOL implanting procedure using instrument 50. Plunger 68 is attached to selecting means 70 by a pair of elongate connecting legs 71 that form a lower part of the pushing member.

As shown, operating pins or rods 62 and 64 are longitudinally disposed in barrel 54 parallel to a longitudinal barrel and instrument axis 72. Piston 66 is disposed in barrel 54 along longitudinal axis 72.

Formed in or included in barrel 54 above adjacent to nozzle 52 is a chamber 74 for holding IOL 44. In this regard, IOL 44 may be retained in chamber 74 by any compatible known manner, such as by a small cartridge (not shown).

By way of illustrative example, with no limitation being intended or implied, barrel 54, which is preferably constructed from stainless steel to enable autoclaving, may have a length, $L_1$, of about 100–120 mm and a diameter, D, of about 25 mm. IOL insertion nozzle, which is preferably constructed of a biocompatible plastic material, may have a length, $L_2$, of about 10 mm and insertion end region 92 may be oval in cross section and be sized (as more particularly described below for being inserted through a ocular incision 53 that is no greater than about 3.7 mm. Pins or rods 62 and 64 may be constructed from about 4 mm diameter stainless steel and piston 66 may be constructed from about 6 mm diameter stainless steel For purposes of clarity, FIG. 3 depicts, in axially exploded format the construction of instrument 50 minus barrel 54.

Figure 3:
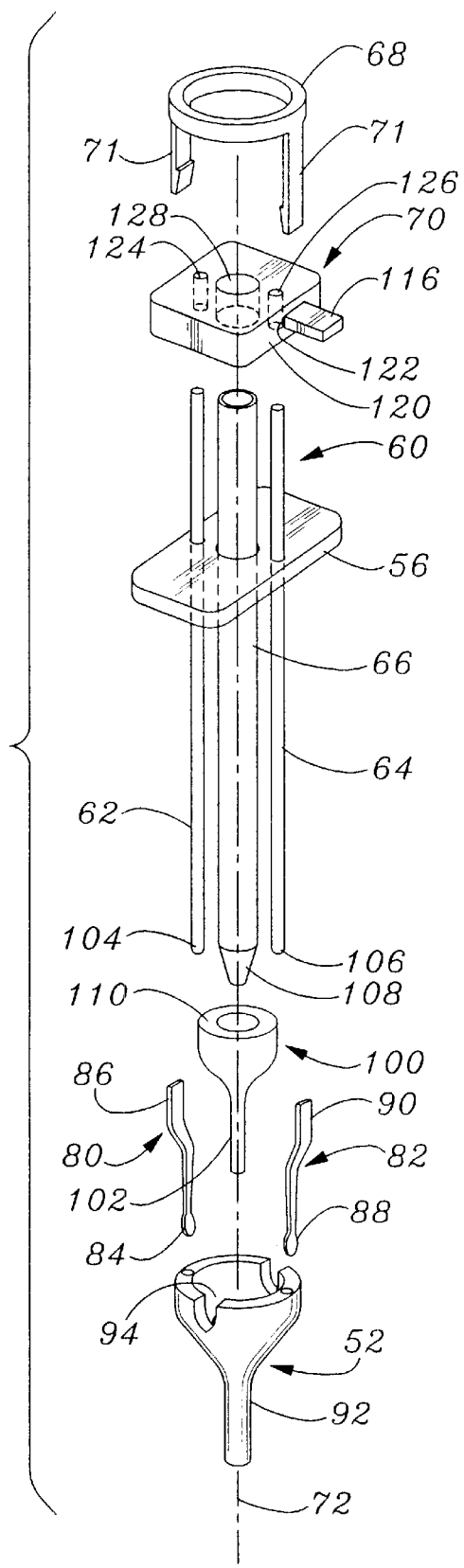
FIG. 3 is an exploded perspective drawing of the intraocular lens implanting instrument of FIG. 2 with the barrel deleted, showing the lens insertion nozzle, an opposed pair of lens shield elements for installation in opposite side regions of the nozzle, a lens pushing member, an elongate piston for attachment to the lens pushing member, a pair of elongate slender pins for attachment to respective ones of the lens shield element, a finger gripping element, a plunger, and connecting means for selectively connecting the plunger to the two slender pins for pushing portions of the shield elements out of the nozzle or to the piston for pushing an intraocular lens out of the nozzle.

In particular, FIG. 3, shows first and second slender IOL shield elements 80 and 82. First shield element 80 is formed having an elastically deformable first protective shield region 84 at a lower (distal) end and a stiff, operating pin-engaging region 86 at an upper (proximal) end. Similarly, second shield element 82 is formed having an elastically deformable second protective shield region 88 at a lower (distal) end and a stiff, operating pin-engaging region 90 at an upper (proximal) end.

Figure 4:
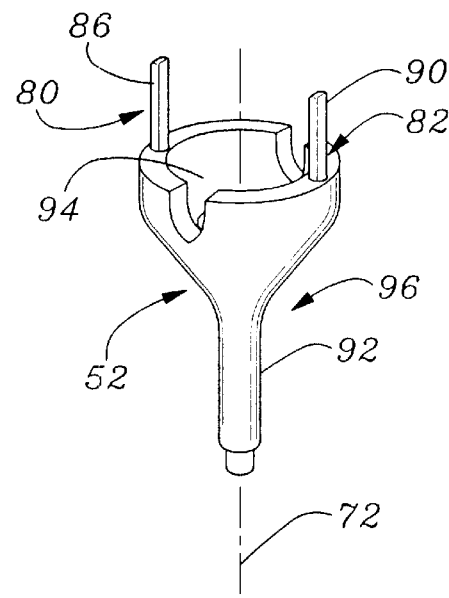
FIG. 4 is a perspective drawing of the lens insertion nozzle showing the installation therein of the two lens shield elements, with upper end regions of the shield elements projecting upwardly from the open upper end of the nozzle.

Although in FIG. 3 first and IOL second shield elements 80 and 82 are shown (for descriptive purposes) separated from nozzle 52. However, for use, first and second shield elements 80 and 82 are, as shown in FIG. 4, installed along opposite internal side regions of nozzle 52. In assembly of first and second shield elements 80 and 82 in insertion nozzle 52 corresponding first and second protective shield regions 84 and 88 are coiled up inside an insertion end region 92 of the nozzle and respective operating pin engagement regions 86 and 90 project upwardly from an open upper end 94 of the nozzle. Thus, first and second shield elements 80 and 82 form with insertion nozzle 52 a nozzle assembly 96 that is preferably disposable after a single use.

It is to be understood that although use of first and second shield elements 80 and 82 are depicted is preferred, in some cases a single shield element, such as either elements 80 and 82, may suffice.

Shown in FIG. 3 included in instrument 50 is an IOL pushing member 100 that is shaped and sized to closely fit into nozzle 52 through nozzle open upper end 94. As such, member 100 is formed having an elongate slender pushing end region 102 hat fits into nozzle insertion end region 92 between coiled protective shield regions 84 and 88.

As further shown in FIG. 3, respective distal ends 104 and 106 of first and second operating pins or rods 62 and 64 are configured for frictionally engaging respective pin engaging regions 86 and 90 of shield elements 80 and 82. Similarly, a tapered distal end 108 of piston 66 is configured for frictionally engaging an upper region 110 of IOL pushing member 100 to enable the axial movement of the pushing member for pushing IOL 44 (FIG. 2) axially through and out of nozzle 52.

Selecting means 70, which selectively connects plunger 68 for operation of shield element operating pins 62 and 64 or operation of IOL pushing piston 66, comprise a generally square block 114 and a selecting member 116 t slidingly installed in a transverse hole 122 through the block between sides 118 and 120 (FIG. 5).

Three parallel, co-planar holes 124, 126 and 128 are formed in block 114 perpendicular to transverse hole 122. As shown in both FIGS. 3 and 5, hole 128 is centrally located along longitudinal axis 72 and is sized to slidingly receive IOL pushing piston 66. Holes 124 and 126 are symmetrically positioned on opposite sides of central aperture 128 and are sized to slidingly receive respective shield element operating pins or rods 62 and 64.

Selecting member 116 is configured (FIG. 5) for frictionally and releasably locking both shield element operating pins 62 and 64 or frictionally locking IOL pushing piston 66 to block 114, and hence to plunger 68, according to the transverse position of the selecting member in block transverse hole 122 as established by the individual using instrument 50. An arcuate pin and piston engaging surface 130 enables the above described selective frictional locking of pins 62 and 64 or piston 66 to block 114.

Figure 5A:
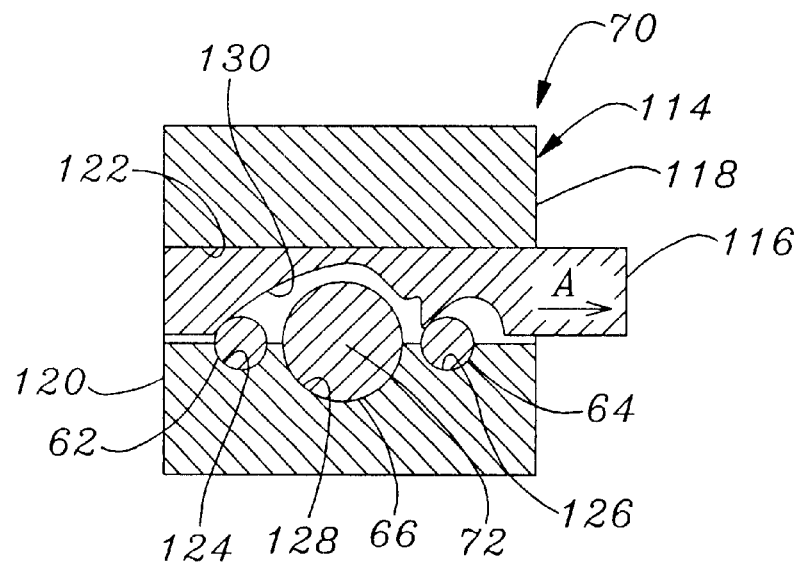
FIG. 5 is a transverse cross sectional drawing of the pin or piston connecting means taken along line 5—5 of FIG. 2, FIG. 5A showing the connecting means configured for connecting the plunger (not shown) to the two lens shield operating pins for moving portions of the lens shield elements axially out from (and back into)the nozzle, and FIG. 5B showing the connecting means configured for connecting the plunger to the lens pushing piston for pushing an intraocular lens axially out of the nozzle.

Selecting member surface 130 is shaped so that when selecting member 116 is pushed outwardly by an operator in the direction of Arrow A to the transverse position shown in FIG. 5A, separate regions of surface 130 frictionally engage both shield element operating pins 62 and 64 where the pins pass through block 114, thereby frictionally locking the pins to the block. This connects plunger 68 to pins 62 and 64 to enable axial movement of both connected shield elements 80 and 82 so that respective protecting regions 84 and 88 can be extended out of nozzle 52, while leaving the block free to slide along IOL pushing piston 66 without moving the piston or IOL 44. This transverse position of selecting member 116 also enables shield element protecting regions 84 and 88 to be withdrawn back into nozzle 52 after IOL 44 has been implanted in an eye and before the nozzle is withdrawn from ocular incision 53 (FIG. 1).

Figure 5B:
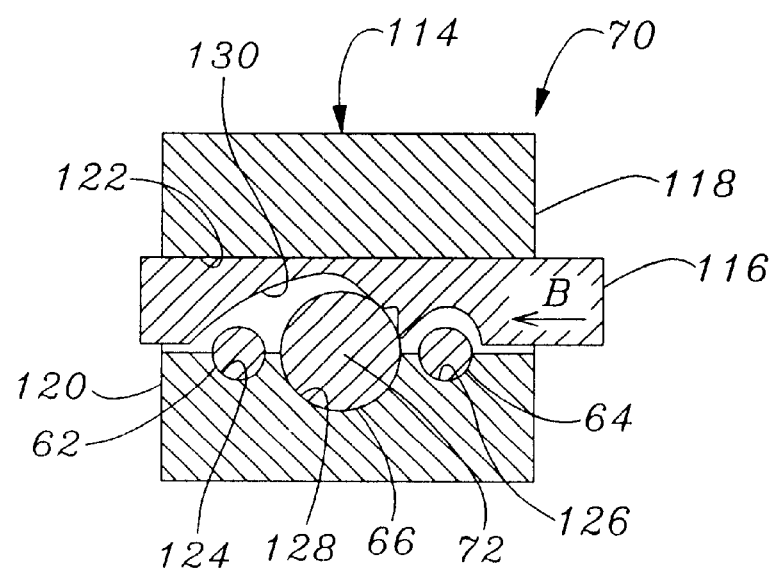

Selecting member surface 130 is further shaped so that when selecting member 116 is pushed inwardly by an operator in the direction of Arrow B to the opposite transverse position shown in FIG. 5B, a different region of surface 130 frictionally engages IOL pushing piston 66 where the piston passes through block 114. This connects plunger 68 to piston 66 to enable the pushing of IOL 44 axially through and out of nozzle 52, while leaving the block free to slide along shield element operating pins 62 and 64 without moving shield element protective regions 84 and 88 from their previously deployed positions.

Figure 6:
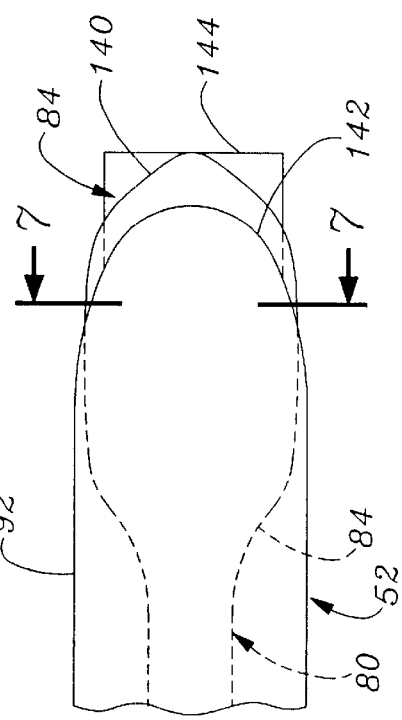
FIG. 6 is plan view of an insertion end region of the lens insertion nozzle showing in broken lines protective shield regions of the lens shield elements disposed in the lens insertion nozzle.

FIG. 6 depicts nozzle insertion end region 92 with protecting region 84 of shield element 80 shown in broken lines curled inside the nozzle insertion end region and with a tip 140 of protecting region 84 extending slightly beyond an arcuate upper end surface 142 of the nozzle insertion end region and over a short, axially extending lower lip 144 of the nozzle end region. Protective region 88 of the other shield element 82 is not shown since it is largely hidden beneath protecting region 84 in FIG. 6. Both protective regions 84 and 88 of respective shield elements 80 and 82 are shown in FIG. 7 curled up curled up inside nozzle insertion end region 92 adjacent a nozzle inner surface 144.

Figure 8:
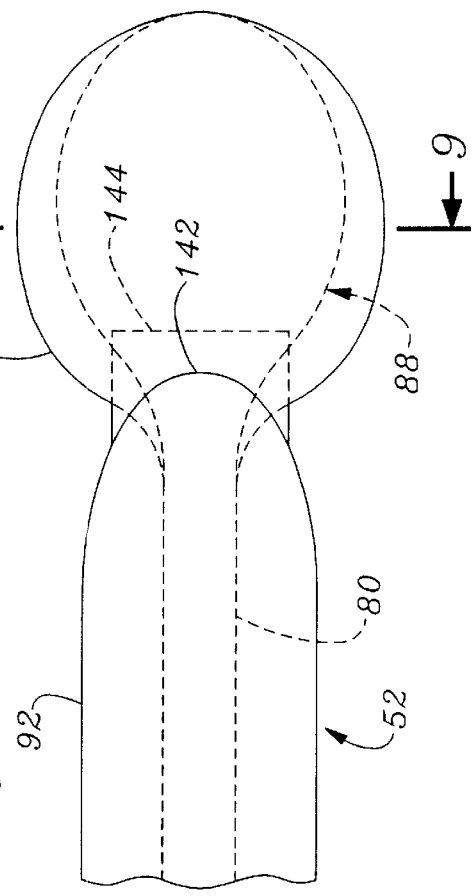
FIG. 8 is plan view of an insertion end region of the lens insertion nozzle showing protective shield regions of the lens shield elements axially extended from the lens insertion nozzle.

FIG. 8 depicts protective region 84 of shield element 80 in its uncurled (un-deformed) axially extended position outside nozzle insertion end region 92. As shown, protective region 84 in plan view is generally paddle- or oval-shaped. Alternatively, uncurled protective region 84 may, in plan view, be circular in shape or square or rectangular in shape with rounded corners. Protective region 88 of shield element 82 is shown in FIG. 8 in broken lines beneath protective region 84, and is shown somewhat smaller than protective region 84 for reasons set forth below. In this regard, it can be appreciated that the principal part of the eye requiring protection during the implanting of IOL 44 in anterior chamber 40 is posterior endothelial surface 36 of cornea 22 (FIG. 1).

It is thus preferred, to minimize protective element occupying space in nozzle insertion end region 92, that the protective region that will, upon IOL implanting, be away from cornea posterior surface 36 and toward iris anterior surface 38 be at least somewhat smaller than the protective region that will be toward the cornea posterior surface. For illustrative purposes herein, protective region 84 is assumed to be the shield element protective region that will be closest to cornea posterior surface 36. Consequently, protective region 84 is shown in FIGS. 7–9 as larger in plan view than protective region 88.

Figure 7:
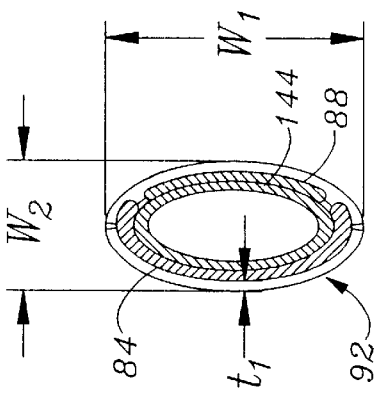
FIG. 7 is a cross sectional drawing taken along line 7—7 of FIG. 6, showing the two lens shield protective shield regions curled inside lens insertion nozzle.
Figure 9:
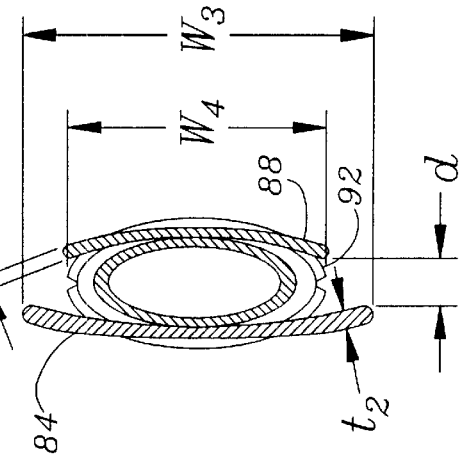
FIG. 9 is a cross sectional drawing taken along line 9—9 of FIG. 8, showing the two lens shield protective shield regions unfolded in their intraocular lens protective positions outside the lens insertion nozzle.

Regarding its size, nozzle insertion end region 92 is shown in FIGS. 7 and 9 as being oval or elliptical in cross section, as is preferred. Nozzle insertion end region 92 preferably has a major width, $w_1$, of no more than about 3.7 mm, a minor width, $w_2$, of no more than about 1.7 mm and a wall thickness, $t_1$, of about 0.15 mm. (FIG. 7). These width dimensions of nozzle insertion end region 92 enable insertion of the nozzle end region through an ocular incision of no greater than about 3.7 mm.

As shown in FIG. 9, protective region 84 has an uncurled (flat) width, $w_3$, of about 5 mm and protective region 88 has a lesser uncurled (flat) width, $w_4$, of about 3.7 mm. Both protective regions 84 and 88 have an uncurled thickness of about 0.15 mm. As a result of protective region 88 being smaller than protective region 84, the two protective regions occupy less space in nozzle end region 92 than would be the case if protective region 88 were the same size as protective region 84.

As shown in FIG. 9, uncurled protective regions 84 and 88 are separated by a distance, d, of about 1.1 mm, which is the spacing provided for unfolding of IOL 44 between the two protective regions.

Because protective region 88 is somewhat smaller than protective region 84, nozzle end lip 144 is sized to support protective region 88 so that the two protective regions overlay one another as depicted in FIG. 8.

For the implanting of some types of deformable IOL's (for example, anterior aphakic IOL's) it may be desirable in instrument 50 to eliminate protective region 88 and shield element 82 while still protecting cornea endothelial surface 36. It may also be desirable to provide a more-rounded nozzle insertion end region 92. Such use of only a single shield element and associated protective region and a more rounded nozzle insertion end region is within the scope of the present invention.

Figure 10:
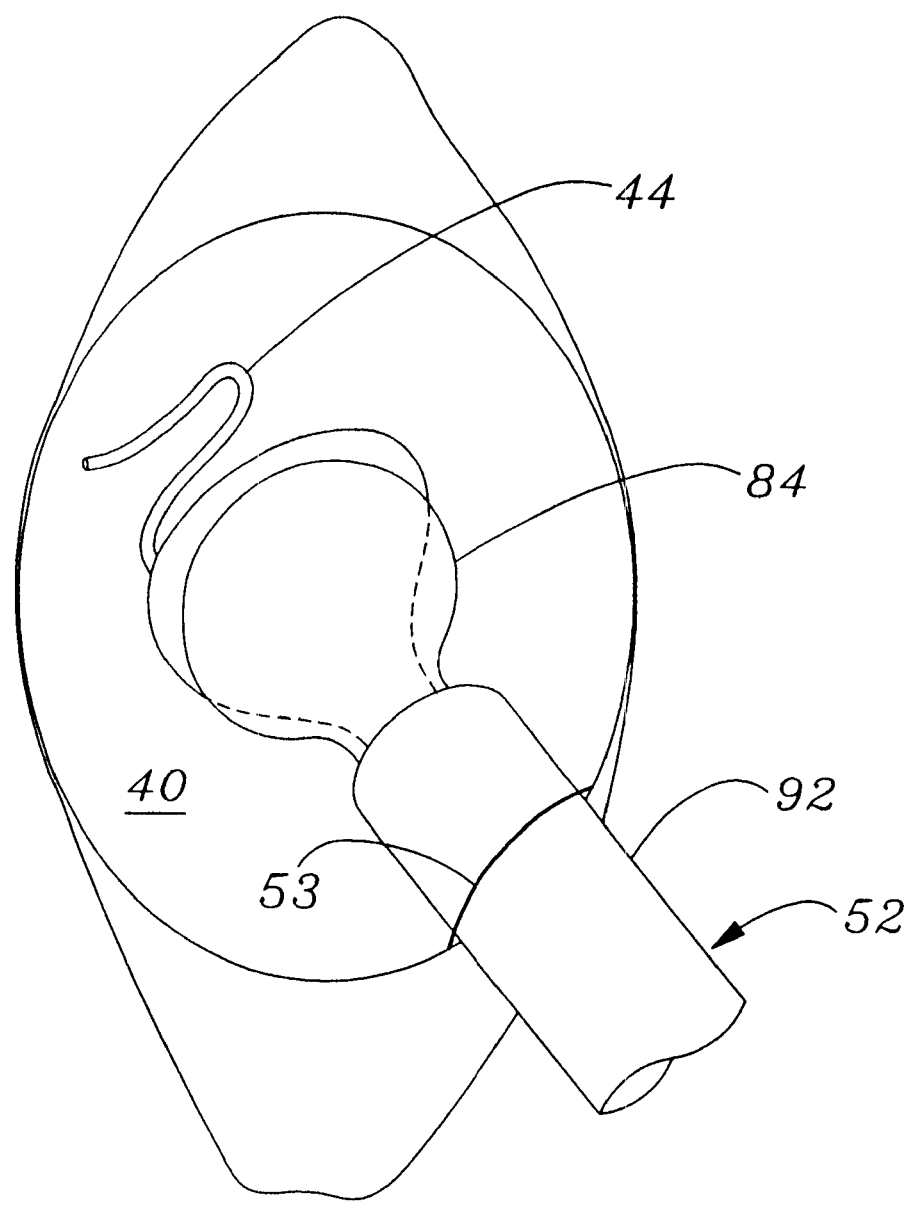
FIG. 10 is a pictorial drawing depicting the process of releasing into the anterior chamber of an eye of an intraocular lens from the lens insertion nozzle between the protective shield regions of the two shield elements.

FIG. 10 depicts IOL 44 in the process of unfolding between protective regions 84 and 88 (shown in broken lines) with nozzle insertion end region 92 inserted into anterior chamber 40 through ocular incision 53.

Operation of IOL Implanting Instrument 50

Although considered readily apparent from the preceding description, operation of IOL implanting instrument 50 is briefly summarized below.

Assume that instrument 50 has been completely assembled in the manner described above, with nozzle assembly 96 (FIG. 4) attached to barrel 54, with operating pins 60 and 62 frictionally connected to respective shield elements shield elements 80 and 82, with piston 66 frictionally connected to IOL pushing member 100, and with IOL 44 installed or located in barrel chamber 74 (FIG. 1).

Assembled IOL implanting instrument 50 is then manipulated so that nozzle insertion end region 92 extends through previously-made corneal incision 53 and into anterior chamber 40 of an eye (FIG. 1).

Transverse selecting member 114 is manually moved by the user in the direction of Arrow A (FIG. 5A) to frictionally lock shield element pins 60 and 62 to block 114 of selecting means 70, and hence to plunger 68.

The instrument user then depresses plunger 68 in the direction of nozzle 52 until protecting regions 84 and 88 of corresponding shield elements 80 and 82 are fully pushed out of nozzle insertion end region 92, with the larger protective region (e.g., protective region 84, as shown in FIGS. 8 and 9) facing cornea posterior surface 36 (FIG. 1).

Next, transverse selecting member is manually moved by the user in the direction of Arrow B (FIG. 5B) to frictionally lock piston 66 to (and unlock shield element pins 60 and 62 from) block 114 of selecting means 70, and hence to plunger 68.

The instrument user then further depresses plunger 68 in the direction of nozzle 52 until IOL pushing member 100 has engaged IOL 44 and has pushed the IOL through nozzle 52 and out of nozzle insertion end region 92 between protective regions 84 and 88. As IOL pushing member 100 pushes IOL 44 into nozzle 52, the IOL becomes forced into an elastically deformed condition. Consequently, as IOL 44 is pushed out of nozzle insertion end region 92 it expands into its original un-deformed shape between protective regions 84 and 88, which control such expansion and protect adjacent ocular surfaces—principally cornea endothelial surface 36—from any erratic movement of the IOL as it expands. Continued depressing of plunger 68 pushes the expanded IOL 44 from between protective regions 84 and 88 and out into anterior chamber 40 for attachment in the chamber by other means (not shown).

As a final step, the user manually moves transverse selecting member 114 back in the direction of Arrow A (FIG. 5A) to frictionally lock shield element pins 60 and 62 to (and unlock piston 66 from) block 114 of selecting means 70, and hence to plunger 68. The instrument user then pulls plunger 68 in the axial direction away from nozzle 52 until protecting regions 84 and 88 of corresponding shield elements 80 and 82 are fully retracted into nozzle insertion end region 92, which can then safely be withdrawn from ocular incision 53.

Although there has been described above an intraocular lens implanting instrument in accordance with the present invention for purposes of illustrating the manner in which the present invention maybe used to advantage, it is to be understood that the invention is not limited thereto. Consequently, any and all variations and equivalent arrangements that may occur to those skilled in the applicable art are to be considered to be within the scope and spirit of the invention as set forth in the claims, which are appended hereto as part of this application.

What is claimed is:

1. An instrument for implanting an elastically deformable intraocular lens in an eye, the instrument comprising:
    a. a hollow tube including an insertion region;
    b. at least one shield element disposed in a deformed condition in the hollow tube; and
    c. a drive assembly positioned relative to the hollow tube and being operable to enable (i) passing the at least one shield element axially out of the insertion region, and (ii) passing an intraocular lens axially out of the insertion region.

2. The intraocular lens implanting instrument as claimed in claim 1, wherein the at least one shield element includes a first shield element and a second shield element.

3. The intraocular lens implanting instrument as claimed in claim 2, wherein the drive assembly enables (i) passing the first and the second shield elements axially out of the insertion region for expanding the shield elements; and (ii) passing the elastically deformed intraocular lens axially out of the insertion region for expanding the lens into an undeformed shape between the first and second shield elements.

4. The intraocular lens implanting instrument as claimed in claim 1, wherein the drive assembly includes at least one actuating pin connected to the at least one shield element.

5. The intraocular lens implanting instrument as claimed in claim 4, wherein the drive assembly includes a piston and an intraocular lens pushing member attached to the piston.

6. The intraocular lens implanting instrument as claimed in claim 5, wherein the drive assembly includes a connector adapted to selectively couple the pushing member to the at least one actuating pin or to the piston.

7. An instrument for implanting an elastically foldable intraocular lens in an eye, the instrument comprising:
    a. a hollow tube including an insertion region adapted to accommodate an intraocular lens in a deformed condition;
    b. first and second shield elements disposed in the hollow tube; and
    c. a drive assembly positioned relative to the hollow tube and being operable to enable (i) passing of the first and second shield elements out of the insertion end region; (ii) passing a deformed intraocular lens out of the nozzle insertion region for expanding into its undeformed state between the first and second shield elements, and (iii) drawing the first and second shield elements back into the insertion region of the hollow tube.

8. The intraocular lens implanting instrument as claimed in claim 7, wherein the first and second shield elements are deformable.

9. The intraocular lens implanting instrument as claimed in claim 8, wherein the first and second shield elements are disposed in the hollow tube in a deformed condition.

10. The intraocular lens implanting instrument as claimed in claim 9, wherein the first and second shield elements are disposed in the hollow tube in a coiled position.

11. The intraocular lens implanting instrument as claimed in claim 10, wherein each of the first and second shield elements is generally paddle shaped in an undeformed condition.

12. The intraocular lens implanting instrument as claimed in claim 7, further comprising a selecting member, operatively connected to the drive assembly, wherein the selecting member is adapted to enable selective passing of the intraocular lens or passing of the first and second shield elements from the hollow tube.

13. The intraocular lens implanting instrument as claimed in claim 7, wherein the shield elements comprise a material selected from a group consisting of silicone and acrylic materials.

14. The intraocular lens implanting instrument as claimed in claim 13, wherein each of the first and second shield elements is generally paddle shaped in an undeformed condition.

15. The intraocular lens implanting instrument as claimed in claim 14, wherein at least one of the shield elements has a width of about 5 mm in the undeformed condition.

16. The intraocular lens implanting instrument as claimed in claim 14, wherein the protective shield regions have a thickness of about 0.15 mm in the undeformed condition.

17. The intraocular lens implanting instrument as claimed in claim 7, wherein the insertion region is sized for insertion through an ocular incision no greater that about 3.7 mm.

18. An instrument for implanting an elastically foldable intraocular lens in an eye, the instrument comprising:
   a. a barrel having proximal and distal ends;
   b. a hollow tube having a insertion region sized for insertion through an ocular incision, the hollow tube being attached to the distal end of the barrel;
   c. a holding chamber defined in the barrel, the holding chamber adapted to accommodate an intraocular lens in a folded condition;
   d. first and second shield elements disposed, in an elastically deformed condition, along opposite sides of the hollow tube; and
   e. a drive assembly positioned relative to the barrel and the hollow tube and being operative to enable (i) passing of the first and second shield elements from the insertion region of the hollow tube, (ii) passing the folded intraocular lens axially out of the insertion region for expanding into an unfolded condition between the first and second shield elements, and (iii) drawing of the shield regions back into the insertion region, the drive assembly further including first and second actuators disposed in the barrel and in engagement with respective ones of the first and second shield elements.

19. The intraocular lens implanting instrument as claimed is claim 18, wherein the drive assembly further includes a piston adapted to push the folded intraocular lens through the hollow tube.

20. The intraocular lens implanting instrument as claimed in claim 18, wherein the shield elements are generally paddle-shaped in an undeformed state.

* * * * *